US012074244B2

(12) United States Patent
Liu et al.

(10) Patent No.: US 12,074,244 B2
(45) Date of Patent: Aug. 27, 2024

(54) OPTICAL SENSOR PACKAGE WITH MAGNETIC COMPONENT FOR DEVICE ATTACHMENT

(71) Applicant: Apple Inc., Cupertino, CA (US)

(72) Inventors: Saijin Liu, San Jose, CA (US); Tongbi T. Jiang, Santa Clara, CA (US); Saahil Mehra, Saratoga, CA (US)

(73) Assignee: Apple Inc., Cupertino, CA (US)

( * ) Notice: Subject to any disclaimer, the term of this patent is extended or adjusted under 35 U.S.C. 154(b) by 535 days.

(21) Appl. No.: 17/473,745

(22) Filed: Sep. 13, 2021

(65) Prior Publication Data
US 2022/0085231 A1 Mar. 17, 2022

Related U.S. Application Data

(60) Provisional application No. 63/078,220, filed on Sep. 14, 2020.

(51) Int. Cl.
H01L 31/167 (2006.01)
A61B 5/00 (2006.01)
(Continued)

(52) U.S. Cl.
CPC .......... H01L 31/167 (2013.01); A61B 5/0059 (2013.01); A61B 5/681 (2013.01);
(Continued)

(58) Field of Classification Search
CPC ..... H01L 31/167; A61B 5/0059; A61B 5/681; A61B 5/256; A61B 2562/166;
(Continued)

(56) References Cited

U.S. PATENT DOCUMENTS 4,913,150 A 4/1990 Cheung et al.
6,313,612 B1 11/2001 Honda
(Continued)

FOREIGN PATENT DOCUMENTS

CN 103876726 6/2014
CN 203943664 11/2014
(Continued)

OTHER PUBLICATIONS

U.S. Appl. No. 17/013,217, filed Sep. 4, 2020, Allec et al.
(Continued)

Primary Examiner — Edwin A. Leon
(74) Attorney, Agent, or Firm — Brownstein Hyatt Farber & Schreck, LLP

(57) ABSTRACT

An integrated sensor package for an electronic device may include a matrix material defining a body structure of the integrated sensor package, a light emitting diode at least partially encapsulated in the matrix material, a photodiode at least partially encapsulated in the matrix material and configured to detect light emitted by the light emitting diode and reflected by an object external to the integrated sensor package, a via structure at least partially encapsulated in the matrix material, a permanent magnet at least partially encapsulated in the matrix material, a first conductive member on a first side of the integrated sensor package and conductively coupling the light emitting diode to a first end of the via structure, and a second conductive member on a second side of the integrated sensor package opposite the first side and conductively coupled to a second end of the via structure.

20 Claims, 9 Drawing Sheets

(51) Int. Cl.
*G04C 10/00* (2006.01)
*G04G 21/02* (2010.01)
*G06F 1/16* (2006.01)
*H02J 50/10* (2016.01)

(52) U.S. Cl.
CPC ........... *G04C 10/00* (2013.01); *G04G 21/025* (2013.01); *G06F 1/163* (2013.01); *H02J 50/10* (2016.02)

(58) Field of Classification Search
CPC ...... G04C 10/00; G04G 21/025; G04G 17/04; G06F 1/163; G06F 1/1635; H02J 50/10
See application file for complete search history.

(56) References Cited

U.S. PATENT DOCUMENTS

| | | | |
|---|---|---|---|
| 6,526,300 B1 | 2/2003 | Kiani et al. | |
| 6,662,033 B2 | 12/2003 | Casciani et al. | |
| 6,882,874 B2 | 4/2005 | Huiku | |
| 7,206,621 B2 | 4/2007 | Aoyagi et al. | |
| 8,463,345 B2 | 6/2013 | Kuhn et al. | |
| 8,948,832 B2 | 2/2015 | Hong et al. | |
| 9,226,663 B2 | 1/2016 | Fei | |
| 9,558,336 B2 | 1/2017 | Lee | |
| 9,597,014 B2 | 3/2017 | Venkatraman et al. | |
| 9,743,838 B2 | 8/2017 | Richards | |
| 9,763,607 B1 | 9/2017 | Acosta et al. | |
| 10,032,557 B1 | 7/2018 | Bossetti | |
| 10,092,197 B2 | 10/2018 | Han | |
| 10,117,587 B2 | 11/2018 | Han | |
| 10,165,954 B2 * | 1/2019 | Lee | A61B 5/681 |
| 10,178,959 B1 | 1/2019 | Homyk | |
| 10,181,021 B2 | 1/2019 | Verkatraman et al. | |
| 10,188,330 B1 | 1/2019 | Kadlec et al. | |
| 10,241,476 B1 | 3/2019 | Moten | |
| 10,278,592 B2 | 5/2019 | Fish et al. | |
| 10,417,513 B2 | 9/2019 | Lee | |
| 10,433,739 B2 | 10/2019 | Weekly et al. | |
| 10,444,067 B2 | 10/2019 | Hsu et al. | |
| 10,485,437 B2 | 11/2019 | Wei et al. | |
| 10,485,478 B1 | 11/2019 | Mirov | |
| 10,537,270 B2 | 1/2020 | Sarussi et al. | |
| 10,586,525 B1 | 2/2020 | Wu et al. | |
| 10,627,783 B2 | 4/2020 | Rothkopf | |
| 10,646,145 B2 | 5/2020 | Pekander et al. | |
| 10,687,718 B2 | 6/2020 | Allec et al. | |
| 10,702,211 B2 | 7/2020 | Clavelle et al. | |
| 10,732,574 B2 | 8/2020 | Shim et al. | |
| 10,736,552 B2 | 8/2020 | Ferber et al. | |
| 10,760,955 B2 | 9/2020 | Chu et al. | |
| 10,918,322 B2 | 2/2021 | Shao | |
| 10,966,643 B1 | 5/2021 | Vavadi | |
| 11,018,524 B2 | 5/2021 | Simpson | |
| 11,076,769 B2 | 8/2021 | Lee | |
| 11,224,381 B2 | 1/2022 | McHale et al. | |
| 11,592,870 B2 * | 2/2023 | Parker | G06F 1/1656 |
| 11,723,563 B1 * | 8/2023 | Shaga | G01K 13/00 600/336 |
| 2015/0054348 A1 | 2/2015 | Akiya | |
| 2015/0099943 A1 | 4/2015 | Russell | |
| 2016/0129279 A1 | 5/2016 | Ferolito | |
| 2016/0278712 A1 | 9/2016 | Sagara | |
| 2017/0095216 A1 | 4/2017 | Laty | |
| 2017/0135633 A1 | 5/2017 | Connor | |
| 2017/0172476 A1 | 6/2017 | Schilthuizen | |
| 2017/0251963 A1 | 9/2017 | Hashimoto et al. | |
| 2018/0344175 A1 | 12/2018 | Rulkov et al. | |
| 2019/0072912 A1 | 3/2019 | Pandya et al. | |
| 2019/0090766 A1 | 3/2019 | Block et al. | |
| 2019/0090806 A1 | 3/2019 | Clavelle et al. | |
| 2019/0167124 A1 | 6/2019 | Verkruijsse et al. | |
| 2020/0163616 A1 | 5/2020 | Sakaya | |
| 2021/0093237 A1 | 4/2021 | Venugopal et al. | |
| 2021/0278561 A1 | 9/2021 | Mehra et al. | |

FOREIGN PATENT DOCUMENTS

| | | |
|---|---|---|
| CN | 109589095 | 4/2019 |
| CN | 109645972 | 4/2019 |
| EP | 3451117 | 3/2019 |
| KR | 20180042472 | 4/2018 |
| WO | WO 19/185903 | 10/2019 |

OTHER PUBLICATIONS

U.S. Appl. No. 17/018,920, filed Sep. 11, 2020, Allec et al.
U.S. Appl. No. 17/018,985, filed Sep. 11, 2020, Shaga et al.
U.S. Appl. No. 17/020,659, filed Sep. 14, 2020, Duan et al.

* cited by examiner

OPTICAL SENSOR PACKAGE WITH MAGNETIC COMPONENT FOR DEVICE ATTACHMENT

CROSS-REFERENCE TO RELATED APPLICATION

This application is a nonprovisional of and claims the benefit under 35 U.S.C. § 119(e) of U.S. Patent Application No. 63/078,220, filed Sep. 14, 2020, the contents of which are incorporated herein by reference as if fully disclosed herein.

FIELD

The subject matter of this disclosure relates generally to electronic devices, and more particularly, to electronic devices with sensing systems that are integrated with magnetic attachment components.

BACKGROUND

Modern consumer electronic devices take many shapes and forms, and have numerous uses and functions. Wearable electronic devices, such as smartwatches and fitness trackers, may provide functions that are particularly suited for devices that are in contact with or otherwise closely coupled to a user's body. For example, smartwatches and fitness trackers may provide workout tracking functions, timekeeping functions, audio (e.g., music) storage and playback functions, biometric sensing functions (e.g., heart rate monitoring), and the like. Such devices may also employ built-in rechargeable batteries so that the devices can be easily charged for frequent use.

SUMMARY

An integrated sensor package for an electronic device may include a matrix material defining a body structure of the integrated sensor package, a light emitting diode at least partially encapsulated in the matrix material, a photodiode at least partially encapsulated in the matrix material and configured to detect light emitted by the light emitting diode and reflected by an object external to the integrated sensor package, a via structure at least partially encapsulated in the matrix material, a permanent magnet at least partially encapsulated in the matrix material, a first conductive member on a first side of the integrated sensor package and conductively coupling the light emitting diode to a first end of the via structure, and a second conductive member on a second side of the integrated sensor package opposite the first side and conductively coupled to a second end of the via structure.

The light emitting diode and the photodiode may be configured to operate as an optical emitter-receiver pair for an optical sensing system. The permanent magnet may define a hole extending through a body of the permanent magnet, the integrated sensor package may further include an electronic component at least partially within the hole defined in the permanent magnet, and the matrix material may extend into the hole defined in the permanent magnet and at least partially encapsulate the electronic component.

The first conductive member may be a first conductive trace, and the second conductive member may be a second conductive trace. The integrated sensor package may further include a first dielectric layer on a first surface of the body structure of the integrated sensor package, and a second dielectric layer on a second surface of the body structure, the second surface opposite the first surface. The first conductive trace may be positioned on the first dielectric layer and the second conductive trace may be positioned on the second dielectric layer. The integrated sensor package may include a third dielectric layer positioned on the second dielectric layer and a third conductive trace positioned on the third dielectric layer and conductively coupled to the second conductive trace. The integrated sensor package may further include a solder ball soldered to the second conductive member.

A wearable electronic device may include a housing member at least partially defining an internal volume of the wearable electronic device, a front cover coupled to the housing member, a display positioned under the front cover, and an integrated sensor package within the internal volume of the wearable electronic device. The integrated sensor package may include a matrix material defining a body structure of the integrated sensor package, an integrated circuit at least partially encapsulated in the matrix material, and a permanent magnet at least partially encapsulated in the matrix material and configured to magnetically attach the wearable electronic device to a docking device external to the wearable electronic device.

The integrated sensor package may further include a light emitting diode at least partially encapsulated in the matrix material, and the integrated circuit may be a photodiode configured to detect light emitted by the light emitting diode and reflected by a wearer of the wearable electronic device. The integrated sensor package may further include a passive circuit component at least partially encapsulated in the matrix material.

The wearable electronic device may further include a rear cover coupled to the housing member and configured to contact a body of the wearer of the wearable electronic device when the wearable electronic device is being worn. The rear cover may define a first surface defining an exterior surface of the wearable electronic device and a second surface opposite the first surface. The integrated sensor package may be attached to the second surface of the rear cover, the light emitting diode may be configured to direct the light through the rear cover, and the photodiode is configured to detect the light through the rear cover.

The wearable electronic device may further include an inductive coil within the internal volume of the wearable electronic device and configured to wirelessly receive power from the docking device, through the rear cover, when the wearable electronic device is magnetically attached to the docking device. The inductive coil may be positioned around an outer periphery of the integrated sensor package.

The light emitting diode and the photodiode may be components of an optical sensing system of the wearable electronic device. The optical sensing system may be configured to detect a heart rate of the wearer of the wearable electronic device.

An integrated sensor package for an optical sensing system of an electronic device may include a matrix material defining a body structure of the integrated sensor package, an array of light emitting diodes positioned around a central region of the body structure, the light emitting diodes of the array of light emitting diodes at least partially encapsulated in the matrix material, an array of photodiodes positioned around the central region of the body structure, the photodiodes of the array of photodiodes at least partially encapsulated in the matrix material, and a permanent magnet positioned in the central region of the body structure and at least partially encapsulated in the matrix material.

The permanent magnet may be a neodymium iron boron magnet, a samarium cobalt magnet, an aluminum nickel cobalt magnet, a ferrite magnet, or the like, having a thickness between about 200 microns and about 2000 microns. The integrated sensor package may further include a substrate at least partially encapsulated in the matrix material and a via extending through the substrate from a first surface of the substrate to a second surface of the substrate. A photodiode of the array of photodiodes may be coupled to the substrate and conductively coupled to the via. The array of light emitting diodes may include a first light emitting diode configured to emit visible light and a second light emitting diode configured to emit infrared light. The integrated sensor package may further include a via structure at least partially encapsulated in the matrix material, a first conductive trace on a first side of the integrated sensor package and conductively coupling a photodiode of the array of photodiodes to a first end of the via structure, and a second conductive trace on a second side of the integrated sensor package and conductively coupled to a second end of the via structure. The integrated sensor package may further include a first dielectric layer between the matrix material and the first conductive trace and a second dielectric layer between the matrix material and the second conductive trace.

BRIEF DESCRIPTION OF THE DRAWINGS

The disclosure will be readily understood by the following detailed description in conjunction with the accompanying drawings, wherein like reference numerals designate like structural elements, and in which.

DETAILED DESCRIPTION

Figure 1A:
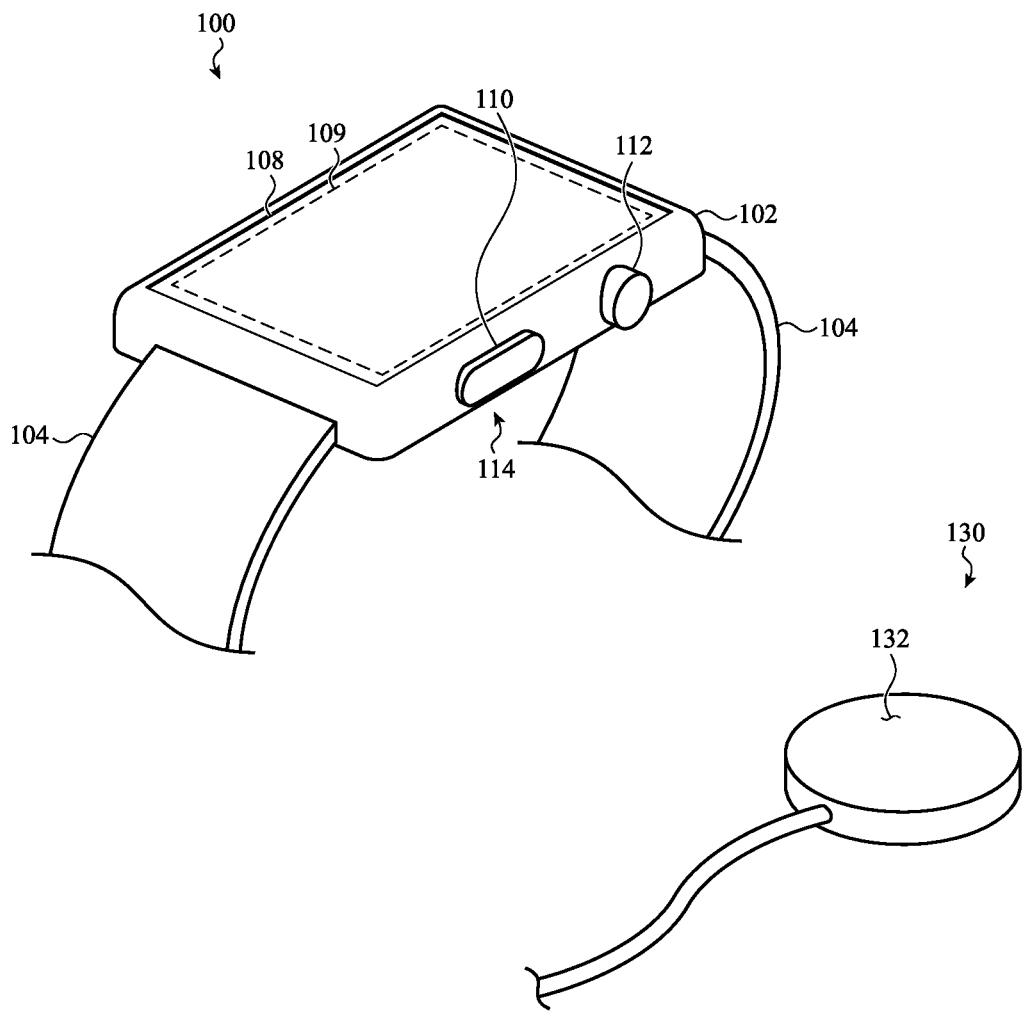
FIGS. 1A-1C depict an example electronic device.

Reference will now be made in detail to representative embodiments illustrated in the accompanying drawings. It should be understood that the following descriptions are not intended to limit the embodiments to one preferred embodiment. To the contrary, it is intended to cover alternatives, modifications, and equivalents as can be included within the spirit and scope of the described embodiments as defined by the appended claims.

Wearable electronic devices may be configured to be attached to (or aligned with) external chargers, such as a charging docks, in order to facilitate recharging so that the devices can be used frequently and without having to replace batteries. Electronic devices as described herein may use magnetic alignment/attachment systems to releasably couple wearable devices to charging docks that can recharge the wearable devices via a wireless connection between the device and the dock.

Because they are intended to be worn for long periods of time and during exercise and other activities, it is beneficial for wearable devices to be small and lightweight. Accordingly, described herein are wearable electronic devices, such as smartwatches, that incorporate various components into a single package to increase packing efficiency in the devices and allow for lighter and smaller devices. In some cases, the particular components that are incorporated together and how they are incorporated together may have a compounding effect on the size and weight reductions that can be achieved. For example, some biometric sensors (such as photoplethysmographs for heart rate sensing, electrodes for ECG sensing, optical systems for pulsatile sensing or other health sensing, and so on) operate better when positioned in close proximity to the rear side of the device so that they have direct optical access to the user's skin. The magnets for aligning or attaching the device to a docking system, therefore, may be positioned further within the device so as to avoid blocking or interfering with the optical sensor and/or components thereof. However, this places the magnet further away from the corresponding magnets or magnetic materials in the docking devices, ultimately reducing the strength of the magnetic attraction between them.

The integrated sensor packages described herein combine components of a rearward-mounted sensing system (e.g., an optical sensor positioned on the rear of the watch) with a magnet for aligning and/or attaching the wearable device to a docking device (referred to herein as an "attachment magnet," although in some embodiments the magnet is used for alignment with a docking device instead of or in addition to attachment to a docking device). In this way, not only can packaging efficiency be increased due to the reduction in the number of different components, but the size of the magnet can be reduced while still producing the same attraction force between the wearable device and a dock. More particularly, integrating the magnet with the rearward-mounted sensing system allows the magnet to be positioned closer to the rear surface of the device, and because the strength of a magnetic field follows an inverse cube law (in which the magnetic field strength varies with the inverse cube of the distance from the magnet), the positioning of the magnet closer to an external surface of the device may allow the use of a smaller magnet while producing the same or greater magnetic attraction to external docking devices.

The integrated sensor package(s) may be formed by encapsulating sensor components, such as photodiodes, light emitting diodes, and the like, as well as a magnet, in a matrix material such as a cured epoxy resin. The matrix material may define the main structural component of the integrated sensor package such that a common, structural circuit board may be omitted from the integrated sensor package. Redistribution layers, which may include dielectric layers and conductive traces, may be applied and/or formed directly on surfaces of the matrix material to facilitate interconnection of the circuit elements in the integrated sensor package and to facilitate interconnection of the integrated sensor package to other components of the device.

While the instant application describes integrated sensor packages with respect to an example type of sensor (e.g., an optical sensing system), it will be understood that other types of sensors or even other components of a device may be integrated with an attachment magnet. For example, components of an electrocardiograph sensor may be integrated with a magnet to form an integrated sensor package. As another example, non-sensor components such as an inductive coil (for wireless charging) may be encapsulated in a matrix material along with an attachment magnet. Other implementations and component integrations are also contemplated.

FIG. 1A depicts an electronic device 100 (also referred to herein simply as a device 100) and a docking device 130 (also referred to herein simply as a dock 130). The device 100 is depicted as a watch, though this is merely one example embodiment of an electronic device, and the concepts discussed herein may apply equally or by analogy to other electronic devices, including mobile phones (e.g., smartphones), tablet computers, notebook computers, head-mounted displays, headphones, earbuds, digital media players (e.g., mp3 players), or the like. The dock 130 may be a charging device to which the device 100 may be magnetically coupled, and which may charge the device 100 via a wireless coupling between the dock 130 and the device 100. While the dock 130 is shown as a round, puck-style charger, this is merely one example embodiment of a docking device, and the concepts discussed herein may apply equally or by analogy to other docking devices, including charging mats, docks, electronic devices with built-in wireless charging functionality (e.g., alarm clocks, another electronic device such as a mobile phone or tablet computer), differently shaped chargers, or the like.

The device 100 includes a housing member 102 and a band 104 coupled to the housing member. The housing member 102 may at least partially define an internal volume in which components of the device 100 may be positioned. The housing member 102 may also define one or more exterior surfaces of the device, such as all or a portion of one or more side surfaces, a rear surface, a front surface, and the like. The housing member 102 may be formed of any suitable material, such as metal (e.g., aluminum, steel, titanium, or the like), ceramic, polymer, glass, or the like. The band 104 may be configured to attach the device 100 to a user, such as to the user's arm or wrist. The device 100 may include battery charging components within the device 100, which may interact with the dock 130 (or other external charging device) to receive power, charge a battery of the device 100, and/or provide direct power to operate the device 100 regardless of the battery's state of charge (e.g., bypassing the battery of the device 100). The device 100 may include a magnet, such as a permanent magnet, that is configured to magnetically couple to a magnet (e.g., a permanent magnet, electromagnet) or magnetic material (e.g., a ferromagnetic material such as iron, steel, or the like) in the dock 130.

The dock 130 may represent an example of an external source of power that may be configured to wirelessly couple (e.g., via inductive coupling) to the device 100 to provide power to the device 100. The device 100 may define a rear surface 114 (e.g., along a rear side of the device opposite a front side or face of the device), and the dock 130 may define a charging surface 132. When the device 100 is placed on the dock 130 so that the rear surface 114 of the device 100 and the charging surface 132 of the dock are in proximity to one another (e.g., in contact), the magnet within the device 100 is attracted to the magnet or magnetic material in the dock 130 to magnetically attach the device 100 to the dock 130. When the device 100 is on the dock 130, a coil of the dock 130 may inductively couple with an inductive coil of the device 100 through the device 100 (e.g., through the rear cover 136 and/or another rear-facing structure), thereby facilitating charging of the device 100 without having to plug a charging cable into a charging port of the device 100. This type of charging operation may be referred to herein as wireless charging of the device 100.

The device 100 also includes a front cover 108, a display 109, input devices such as a crown 112 and a button 110, a haptic actuator, and other components. Such components are described herein.

Figure 1B:
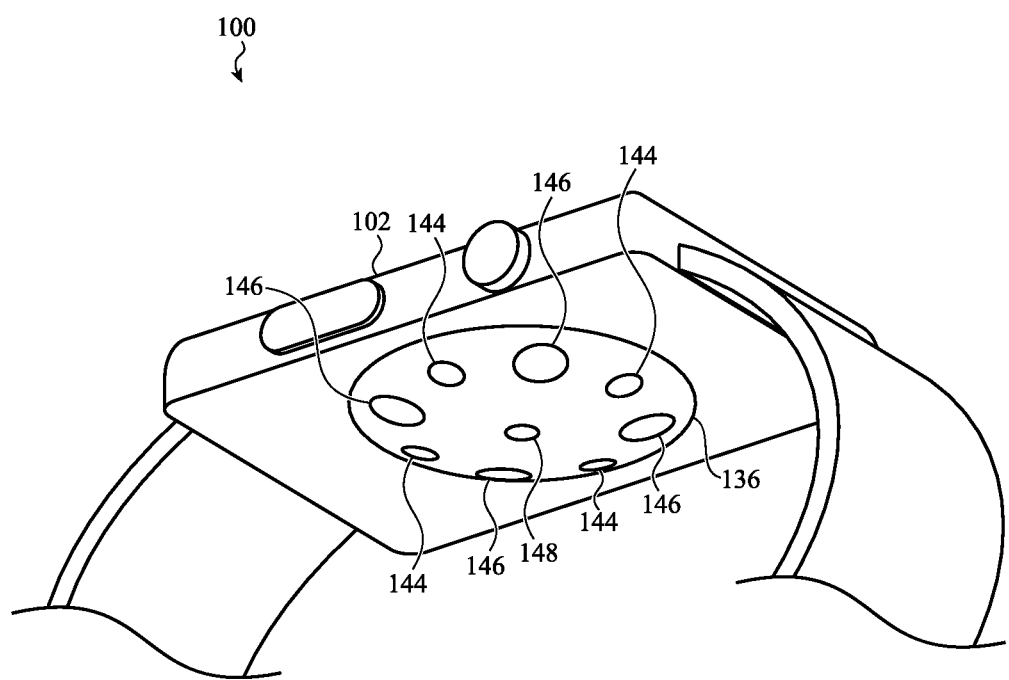
Figure 1C:
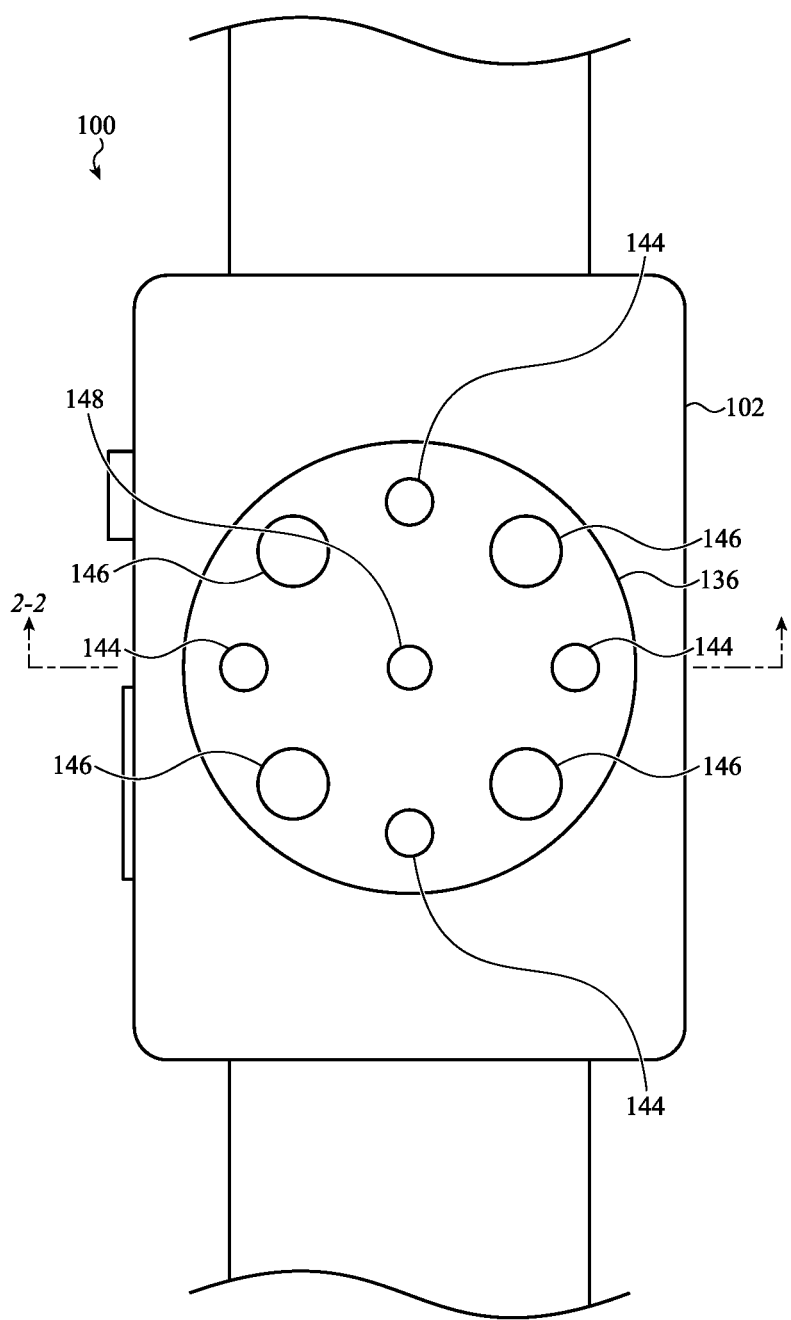

FIGS. 1B and 1C show a rear side of the device 100. The device 100 includes a rear cover 136 coupled to the housing member 102 and defining at least a portion of the rear exterior surface of the device 100. The rear cover 136 may be formed of or include any suitable material(s), such as sapphire, polymer, ceramic, glass, or any other suitable material.

The rear cover 136 may define a plurality of windows to allow light to pass through the rear cover 136 to and from sensor components within the device 100. For example, the rear cover 136 may define emitter windows 148 and 144 and receiver windows 146. The emitter and/or receiver windows 144, 146, 148 may be defined by the material of the rear cover 136 (e.g., they may be light-transmissive portions of the material of the rear cover 136), or they may be separate components that are positioned in holes formed in the rear cover 136. A mask or coating may be applied to the rear cover 136 to define masked regions, and the emitter and/or receiver windows 144, 146, 148 may correspond to unmasked or differently masked regions of the rear cover 136 (e.g., holes in an opaque mask). The mask may be optically transparent, transparent to infrared light, transparent to ultraviolet light, or otherwise selectively transparent to permit wavelengths of light emitted from emitters beneath the emitter windows 144, 148 to penetrate the mask and reach receivers beneath the receiver windows 146. In some embodiments, the receiver windows 146 may be invisible to the human eye but pass light from the emitters, insofar as they are covered by an optically opaque mask that is transmissive within the wavelengths of light emitted by the emitter(s).

The emitter windows 148, 144 may be aligned with or otherwise configured to pass light emitted by emitters, such as light emitting diodes in an integrated sensor package. The emitted light may be any suitable type of light for facilitating sensing functions, and may include visible light, infrared light, or the like. The receiver windows 146 may be aligned with or otherwise configured to pass light onto sensors, such as photodiodes, in the integrated sensor package. The light that passes through the receiver windows 146 and is incident on the sensors may be light that is emitted by the light emitters (e.g., through the emitter windows 144, 148) and reflected by the body of the user (or whatever object is the target of the sensor). For example, the light from the emitters may be directed onto the skin of a user's wrist. Some portion of the light may be absorbed or scattered, while another portion of the light may be reflected towards or otherwise be detected by the sensors of the integrated sensor package. Characteristics of the light detected by the sensors (e.g., the intensity or amount of detected light) may be used to determine biometric information such as heart rate, blood oxygen concentrations, and the like, as well as information such as a distance from the device to an object. In some cases, the emitter and receiver windows 144, 146, 148 may include filters, coatings, lenses, or the like, to condition the light that is emitted and/or received through the windows.

The particular arrangement of windows in the rear cover 136 shown in FIG. 1B is one example arrangement, and other window arrangements (including different numbers, sizes, shapes, and/or positions of the windows) are also contemplated. As described herein, the window arrangement may be defined by or otherwise correspond to the arrangement of components in the integrated sensor package.

The rear cover 136 may also be configured to contact the dock 130 when the device 100 is attached to the dock 130. A magnet within the device 100 may magnetically couple to a magnet or magnetic material in the dock 130. The rear cover 136 may be formed from a nonconductive material that does not significantly impede or reduce magnetic flux.

Figure 2:
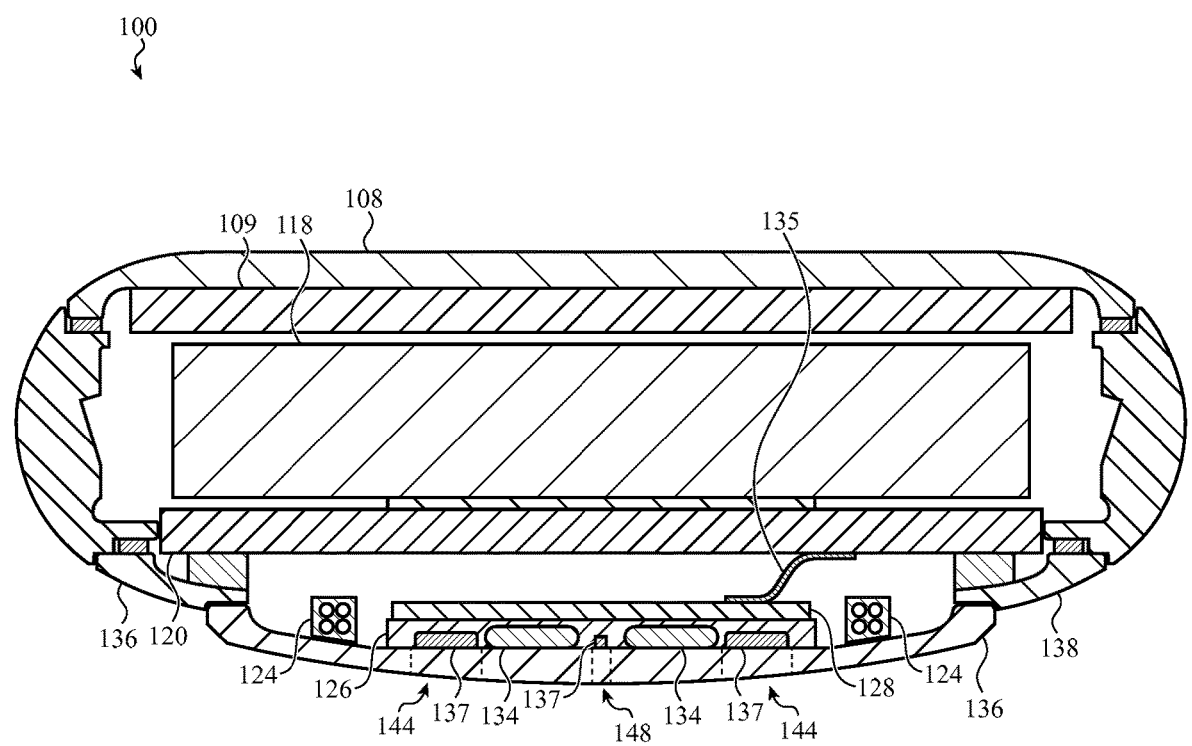
FIG. 2 depicts a partial cross-sectional view of the example electronic device of FIGS. 1A-1C.

FIG. 2 is a partial cross-sectional view of the device 100, viewed along line 2-2 in FIG. 1C. FIG. 2 illustrates an example arrangement of components within the device 100. Some components and structures of the device 100 may not be shown in FIG. 2 for simplicity, though it will be understood that additional components and structures may be present in the device 100.

As noted above, the device 100 includes a housing member 102 to which a front cover 108 is coupled. A display 109 may be positioned below the front cover and configured to display graphical outputs that are visible through the cover 108. The device may also include a battery 118 which provides electrical power to the device, and which may be recharged by a charging system that includes an inductive coil 124. The inductive coil 124 may be positioned proximate the interior surface of the rear cover 136 (which may be opposite the exterior surface of the rear cover 136) and configured to inductively couple to a coil in a dock or wireless charger (e.g., the dock 130, FIG. 1A).

As shown in FIG. 2, the rear cover 136 may be attached to a rear housing member 138, which is in turn attached to the housing member 102. Accordingly, the rear housing member 138 may define a first portion of a rear surface of the device 100, and the rear cover 136 may define a second portion of the rear surface of the device 100. The rear housing member 138 may be formed from any suitable material, such as plastic, glass, sapphire, metal, ceramic, or the like.

The device 100 may also include a logic board 120. The logic board 120 may include a substrate, and processors, memory, and other circuit elements coupled to the substrate. The logic board 120 may be wholly or partially encapsulated to reduce the chance of damage due to an ingress of water or other fluid. The logic board 120 may provide processing and other electrical functions of the device.

The device 100 may also include an integrated sensor package 126, which may be attached to the interior surface of the rear cover 136. The integrated sensor package 126 may include sensor components 137 and one or more magnets (e.g., a magnet 134, FIG. 2) at least partially encapsulated in a matrix material, which forms a body structure of the integrated sensor package 126 and structurally retains the sensor components 137 and the magnet 134 together in a single integrated assembly.

In some cases, the sensor components 137 correspond to light emitters, and may be aligned with or positioned proximate the emitter windows 144 and 148 (as shown in FIG. 2). Light emitted by the sensor components 137 may pass through the emitter windows 144 and 148 and, when the device is being worn, be incident on the user's body. As shown, the emitter windows 144 and 148 are defined by transparent portions of the rear cover 136. In some cases, the size and shape of the emitter windows 144 and 148 (and the receiver windows) may be defined at least in part by an opaque mask (e.g., ink, dye, films, coatings, metallized layers, etc.) formed on or applied to the rear cover 136. While the instant application describes the windows as sensor or receiver windows, and includes sensor components such as light emitters and light receivers, it will be understood that other types of sensing components may be used in an integrated sensor package, and in such circumstances the windows may provide different functions, may be differently configured, and/or may not be used at all. For example, in some cases an integrated sensor package may include components of an electrocardiograph, such as electrodes that are configured to contact a user's skin. In such cases, the electrodes may be part of the integrated sensor package, and may extend through holes in the rear cover or otherwise have access through the housing structure of the device to access the user's skin.

The integrated sensor package 126 may be attached to a circuit board 128 (e.g., via a ball grid array or other conductive coupling), which may be conductively coupled to the logic board 120 via a conductive component 135 (e.g., a flexible circuit element). Other electrical components of the device 100 may also be attached to or conductively coupled to the circuit board 128.

Figure 3A:
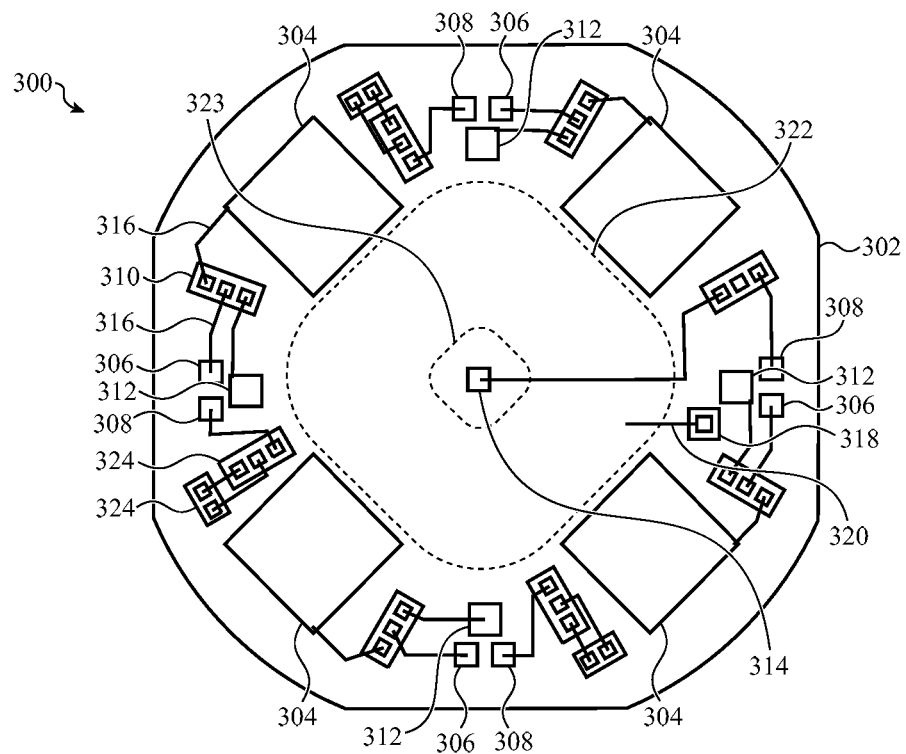
FIGS. 3A-3B depict top views of an example integrated sensor package.

FIG. 3A illustrates an example integrated sensor package 300, which may be an embodiment of the integrated sensor package 126, and may be part of an optical sensing system. The optical sensing system may be used to detect a distance between the integrated sensor package 300 (or the device housing the package) and an external object (such as a body part of a person), to sense fluid flow within an object (such as blood flow within a limb or digit), to detect temperature of an object, and so on. FIG. 3A shows the surface of the integrated sensor package 300 that is configured to face the interior surface of the rear cover of a device. More particularly, the depicted surface of the integrated sensor package 300 may include optical components, such as photodiodes, light emitting diodes, etc., that are configured to transmit and/or receive light through the windows of the rear cover.

As shown in FIG. 3A, the integrated sensor package 300 may include a matrix material that defines a body structure 302 of the integrated sensor package 300. The matrix material may be a cured epoxy or other suitable polymer material. The body structure 302 may be formed by flowing an epoxy (or other suitable curable material in a flowable state) onto an arrangement of components such that the epoxy at least partially encapsulates the components, and then allowing the epoxy to cure. The cured epoxy may form a rigid body structure 302 that retains the components together and provides structural integrity to the integrated sensor package 300. The process of forming an integrated sensor package, including flowing an epoxy or other curable material onto the components of the package, is described with respect to FIGS. 6A-6F.

The integrated sensor package 300 may include integrated circuits (e.g., integrated circuit dies) that are part of the sensing system and are at least partially encapsulated in the matrix material. The specific type of integrated circuits may depend on the type of sensor or other component that is being formed into an integrated package. In the case of the integrated sensor package 300, which may be an optical sensing system, the integrated circuits may include photodiodes (e.g., photodiodes 304), light emitting diodes (LEDs) 306, 308, 312, and 314, or the like. The LEDs 306, 308, 312, and 314 may be configured to emit light onto a user's body (through the rear cover), and the photodiodes 304 may be configured to sense or detect light from the LEDs that is reflected by the user's body. The photodiodes and LEDs of the integrated sensor package 300 may operate as optical emitter-receiver pairs for the optical sensing system. The photodiodes need not be functionally linked to any specific LEDs, as the LEDs may provide a flood-style illumination that may be detected by any of the photodiodes. In some cases, however, a photodiode may be functionally linked to one or more specific LEDs and configured to detect light only from those LEDs.

The photodiodes 304 may be arranged in an array of photodiodes 304 positioned around a central region of the body structure 302. For example, as shown in FIG. 3A, four photodiodes 304 may be positioned in a radial array about the central region. Light emitting diodes may also be arranged in an array of LEDs positioned around the central region of the body structure 302. For example, as shown in FIG. 3A, LEDs 306, 308, and 312 may be positioned in radial arrays about the central region of the body structure 302. The LEDs 306, 308, and 312 may be positioned proximate each other in groups, and as such the array of LEDs may be understood as an array of LED groups. In some cases one or more additional LEDs are also included in the integrated sensor package 300. For example, an LED 314 may be positioned at or proximate a center of the body structure 302.

Figure 3B:
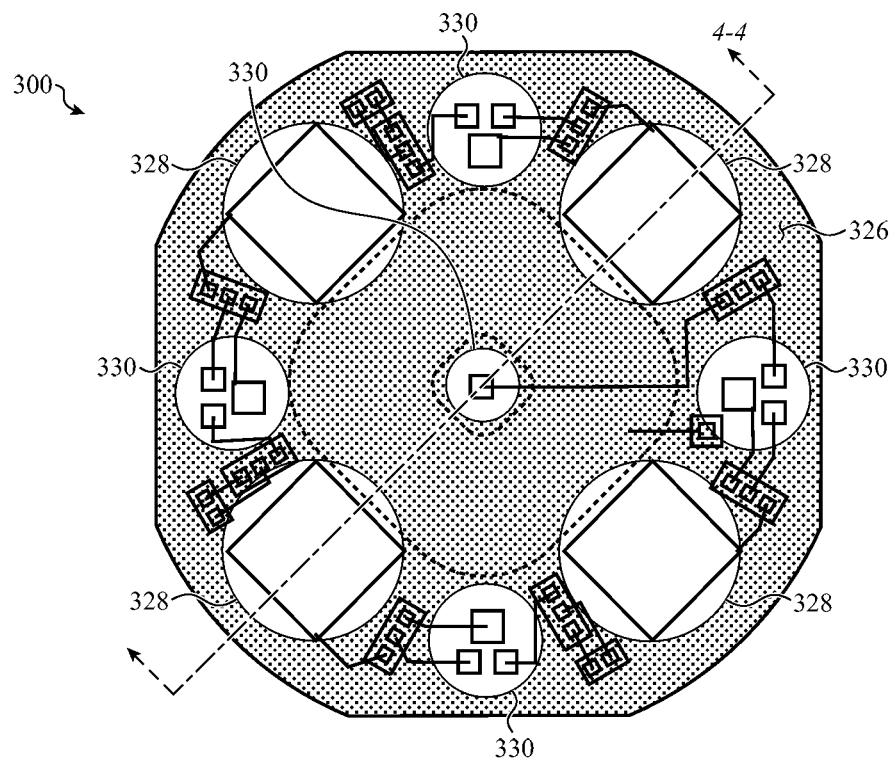

The LEDs 306, 308, 312, and 314 may be configured to emit light having particular wavelengths, colors, and/or other characteristics. For example, the LEDs 306 may emit red light, the LEDs 308 and 314 may emit infrared light, and the LEDs 312 may emit green light. The particular wavelengths, colors, and/or other characteristics of the LEDs may be selected for the particular type of sensor and/or photodiodes being used, the type of sensing provided by the integrated sensor package 300, or other factors. Although particular shapes and positions of the LEDs are shown, it should be appreciated that such shapes and positions (as well as relative positions) of the LEDs may vary in embodiments without departing from the spirit or scope of this document. Accordingly, the particular configurations shown in FIGS. 3A and 3B are illustrative rather than necessarily limiting.

The radial arrays of LEDs may provide a large, relatively homogenous or continuous area of illumination, while the radial array of photodiodes may help cover a large area of potential sensing locations. In some cases, by providing multiple emitters and receivers, the integrated sensor package can accommodate misalignments between the rear surface of the device and the wearer's skin. For example, in a smartwatch implementation, at least one of the photodiodes (or the window region corresponding to that photodiode) is likely to be flush against (or near) the user's skin even during movement of the user and/or the smartwatch or if the smartwatch is loose. While FIG. 3A illustrates one example arrangement of LEDs and photodiodes, the locations of the arrays of photodiodes and LEDs (and the position of the individual components in those arrays) may differ from those shown in FIG. 3A.

The integrated sensor package 300 may also include other components at least partially encapsulated in the matrix material. For example, the integrated sensor package 300 may include via structures (such as the via structures 310), surface-mount circuit components, or the like. Components of the integrated sensor package 300 may be electrically coupled together via electrically conductive members, such as the conductive traces 316. The conductive traces 316 may be electrically conductive materials that are deposited or otherwise formed on the integrated sensor package 300. For example, the conductive traces 316 may be formed on or in conjunction with dielectric layers that are formed on surfaces of the body structure 302. The conductive traces 316 may be formed from copper, gold, silver, or any other suitable electrically conductive material.

The integrated sensor package 300 may also include one or more permanent magnets, such as the permanent magnet 322. FIG. 3A shows the outline of the permanent magnet 322 in broken lines, as the permanent magnet 322 may be within the matrix material and/or covered by dielectric layers that are formed on the surfaces of the matrix material. The permanent magnet 322 may be configured to magnetically attach an electronic device to a docking device external to the electronic device, as described above. The permanent magnet 322 may be formed of any suitable material, such as neodymium iron boron, samarium cobalt, aluminum nickel cobalt, ferrite, or the like. In some cases, the permanent magnet 322 is coated or covered with a coating such as an epoxy coating (which may be black). The permanent magnet 322 in FIG. 3A (as well as the magnet 134 in FIG. 2, the permanent magnet 522 in FIG. 5, or other magnets depicted in the figures) may represent a single magnet or multiple magnets (e.g., two or more discrete magnets). In the case where multiple magnets are used, they may be positioned in an array or other arrangement in the same area within the integrated sensor package as the magnets shown in the figures, or elsewhere in the integrated sensor package 300.

The use of multiple magnets may allow a high level of system packing efficiency, because a given attractive force (e.g., between the device 100 and the docking device 130) may be achieved without requiring a single continuous volume within the integrated sensor package 300 for a single magnet. For example, the individual magnets (each of which may be smaller than a single magnet that provides an attractive force equivalent to the combined force of the individual magnets) may be strategically placed in the integrated sensor package 300 at locations that would otherwise be unoccupied (e.g., where photodiodes, LEDs, or other components of the integrated sensor package 300 are not located). Additionally, the relative positioning of the individual magnets may be used to shape the magnetic field provided by the integrated sensor package 300. In some instances, the individual magnets may be positioned as close to the center of the integrated sensor package 300 as possible, which may improve the attachment force to a peripheral device such as the docking device 130 (e.g., by concentrating the magnetic force in a single central area). Additionally or alternatively, the individual magnets may be symmetrically positioned in the integrated sensor package 300 (e.g., symmetric across one or more axes, in a radially symmetric arrangement, or the like).

The permanent magnet 322 may define a hole 323 extending through a body of the permanent magnet 322 (or, in the case of multiple magnets, they may be arranged to define a hole or unoccupied space in the area of the hole 323 in FIG. 3A). An electronic component, such as the LED 324, may be positioned in the hole 323, and the matrix material may extend into the hole and at least partially encapsulate the electronic component, as shown in greater detail in FIG. 4. In some cases, a different component, such as a different LED, a photodiode, or other component, may be positioned in the hole 323. In an implementation where multiple discrete magnets are used, the magnets may be arranged around a central area in which an electronic component, such as the LED 324, may be positioned.

In some cases, the permanent magnet 322 (or multiple permanent magnets) may be electrically grounded to an electrical ground plane of a device. In such cases, a conductive trace 320 may be conductively coupled to a surface of the permanent magnet 322 and to a via structure 318, which may be conductively coupled to a ground plane of a device (e.g., via a ball grid array on an opposite side of the integrated sensor package 300). Grounding the permanent magnet 322 may result in the permanent magnet 322 functioning as an electromagnetic shield (e.g., shielding internal components of a device from electromagnetic interference), and/or may help reduce electrical crosstalk between the permanent magnet 322 and other circuitry of the integrated sensor package 300 and/or the device.

The permanent magnet 322 may have a thickness between about 200 microns and about 2000 microns. In some cases, the permanent magnet 322 has a thickness between about 400 microns and about 700 microns, or between about 450 microns and about 650 microns. In some cases, the permanent magnet 322 has a thickness less than about 650 microns, or less than about 500 microns. Where multiple permanent magnets are used, they may all have the same thickness, or they may have different thicknesses. In some cases, magnets having a thickness below about 700 microns (and optionally below about 500 microns) is feasible due to the proximity of the permanent magnet 322 to the rear cover of a device. For example, if the permanent magnet were located above a sensor package (rather than integrated with the sensor package as described herein), a larger magnet may be required to provide sufficient force for aligning and/or attaching the device to a docking device. For example, in order to produce the same alignment and/or attachment force as the permanent magnet 322, a permanent magnet that is not integrated in an integrated sensor package (and is instead positioned above the circuit board 128 in FIG. 2, for example) may require a thickness greater than about 1.0 mm. Accordingly, the integration of the magnet into the integrated sensor package may facilitate the use of smaller (e.g., less than about 700 microns) magnets. The use of a smaller magnet may allow for the inclusion of other components into the device without changing the outside dimensions of the device, or make more internal space for larger components (e.g., a larger battery) without changing the outside dimensions of the device.

As shown in FIG. 3A, the permanent magnet 322 may have a generally square shape, with an outer periphery having four sides (which may be straight or substantially straight). The photodiodes and LEDs may be arranged around the outer periphery of the permanent magnet 322. For example, the photodiodes 304 may be positioned adjacent the sides of the permanent magnet 322, and the LEDs (e.g., the LEDs 306, 308, 312) may be positioned adjacent the corners of the permanent magnet 322. The corners of the permanent magnet 322 may be rounded or curved, as shown, or they may be sharp (e.g., a 90 degree corner where two straight sides meet). The shape of the permanent magnet 322 may vary in different embodiments and need not be generally square; it may be rectangular, circular, oval, irregular, have more or fewer sides than four, and so on.

FIG. 3B illustrates the integrated sensor package 300 with a mask 326 on a surface of the integrated sensor package 300. The mask 326 may be an opaque mask, and may be formed of ink, dye, solder mask materials, epoxy, sheets or films, coatings, or the like. The mask 326 may be a single layer of material, or multiple layers. The mask 326 may define holes 328 that are positioned over the photodiodes, and holes 330 that are positioned over the LEDs. The holes 328, 330 may allow optical access for the photodiodes and LEDs, while the mask 326 helps prevent optical crosstalk between the LEDs and photodiodes. For example, the mask 326 may prevent or limit light from the LEDs from being detected by the photodiodes before the light has been directed onto a user's skin and reflected back onto the photodiodes. The mask 326 may also prevent optically inactive components of the integrated sensor package 300 (e.g., the body structure 302, conductive traces, vias, etc.) from being visible through the rear cover of a device. As mentioned above, the mask 326 may extend over one or both of the photodiodes or the LEDs, thereby eliminating one or both of the holes 328, 330.

Figure 4:
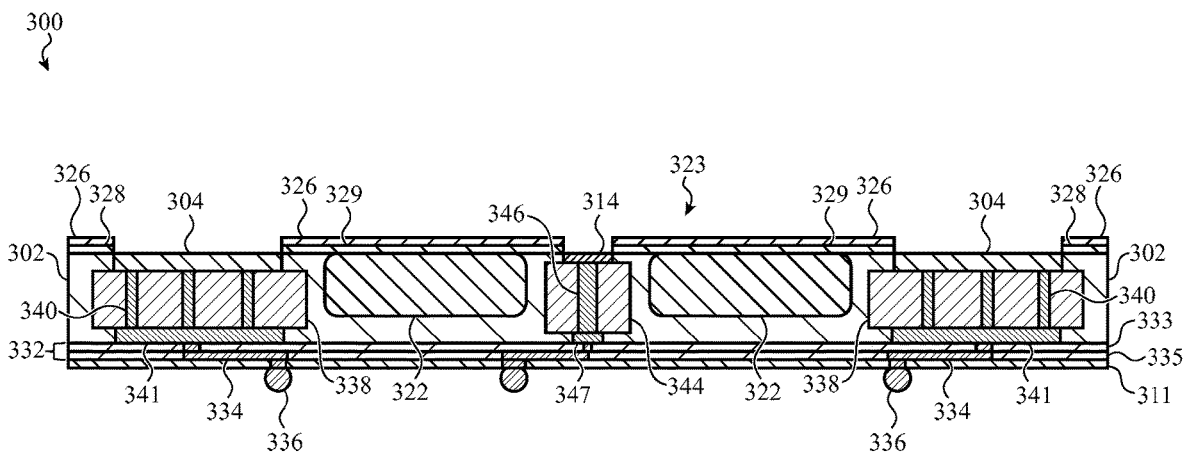
FIG. 4 depicts a partial cross-sectional view of the integrated sensor package of FIGS. 3A-3B.

FIG. 4 is a partial cross-sectional view of the integrated sensor package 300, viewed along line 4-4 in FIG. 3B. FIG. 4 illustrates example configurations of the components of the integrated sensor package 300 and how the components are at least partially encapsulated in the matrix material that forms the body 302.

The photodiodes 304, which may be or may include semiconductor dies, may be coupled to carriers 338. The carriers may include conductive vias 340 that extend through the carriers from a first surface, where a photodiode 304 is mounted, to a second surface, where a conductive pad 341 is mounted. The carriers 338 may each include multiple conductive vias, which may increase thermal coupling between the photodiodes 304 (or other semiconductor on the carriers 338) to the conductive pads 341. The conductive vias may be formed from any suitable conductive material, such as gold, copper, silver, or the like, and the carriers may be formed of a ceramic, such as $Al_2O_3$ (aluminum oxide), AlN (aluminum nitride), silicon, or the like. The photodiodes 304 may be attached to the carriers 338 via a solder or conductive adhesive, such as an AuSn solder, a silver epoxy, or the like. The conductive pads 341 may be copper, gold, or any other suitable conductive material. The conductive vias 340 and pads 341 may allow conductive coupling to the photodiodes 304 from a bottom surface of the integrated sensor package 300, which may include a redistribution layer 332 that can be soldered to a circuit board to conductively couple the integrated sensor package 300 and its components to other electrical components of a device.

Other electrical components in the integrated sensor package 300 may have a similar construction to the photodiode assemblies. For example, FIG. 4 illustrates the LED 314, which is positioned in a hole 323 defined through the permanent magnet 322. The LED 314, which may be or may include a semiconductor die, may be coupled to a carrier 344. The carrier 344 may include one or more conductive vias 346 that conductively couple the LED 314 to a conductive pad 347 (which in turn may be conductively coupled to conductive traces of a redistribution layer 332). The materials of the carrier, conductive pads, vias, and the die attach (the material for coupling the semiconductor die to the carrier) may be the same for the LED assembly as for the photodiode assembly. Other components of the integrated sensor package 300, such as the LEDs 306, 308, 312, and/or other electrical components, may have the same or a similar construction.

The optical components of the integrated sensor package 300 may be exposed along the top surface of the integrated sensor package 300, or otherwise positioned near the top surface, so that light can be emitted and/or received by the components. As used herein, the terms top and bottom are used in reference to the orientation of the component in the figure being discussed, and does not necessarily correspond to the final orientation of a component when integrated into a device. For example, the "top" of the integrated sensor package 300 as shown in FIG. 3A (e.g., the portion facing out of the page) may be positioned along a rear cover of a smartwatch.

The components may also be conductively coupled to the redistribution layer 332 on the bottom surface of the integrated sensor package 300. However, the semiconductor dies of the various optical components may not be the same thickness. In order to produce an integrated sensor package having a substantially uniform thickness, the thicknesses of the carriers and/or conductive pads may be varied so that each assembly has substantially a same height. Thus, as shown in FIG. 4, for example, the photodiodes 304 have a greater thickness than the LED 314. Accordingly, the carrier 344 for the LED 314 may be thicker than the carrier 338 for the photodiodes 304. In this way, the integrated sensor package 300 may have a uniform or substantially uniform thickness, while the LED 314 and photodiode 304 may be correctly positioned along the top surface of the integrated sensor package 300. (In the case of components that do not need to be flush with or close to the top surface, those assemblies may be thinner.)

As noted above, the ability to mount the permanent magnet 322 closer to the rear cover of a device (or whichever surface of the device couples to, or aligns with, an external docking device) allows the use of a thinner and/or less powerful magnet, while still providing the same magnetic coupling strength of a thicker magnet that is positioned further from the rear cover. Thus, incorporating the permanent magnet 322 into the same package as the optical sensor affords a more rearward positioning of the permanent magnet 322 than would otherwise be achieved. In order to further maximize the rearward positioning of the permanent magnet 322, the permanent magnet may be biased towards the top surface of the integrated sensor package 300, as shown in FIG. 4. In some cases, a surface of the permanent magnet 322 is flush with the top surface of the body structure 302 of the integrated sensor package 300.

As noted above, the integrated sensor package 300 may include a redistribution layer 332 on a bottom side of the integrated sensor package 300. The redistribution layer 332 may include one or more dielectric layers (e.g., dielectric layers 333, 335), which may be passivation layers, as well as conductive traces 334. The conductive traces 334 may be conductively coupled to the conductive pads of the photodiode assemblies, LED assemblies, or other components of the integrated sensor package 300, and may also be conductively coupled to solder balls 336 (or solder pads or other conductive materials) that are exposed along the bottom side of the integrated sensor package 300. The redistribution layer 332 may allow the conductive connections to the components of the integrated sensor package 300 to be rearranged as compared to their locations within the integrated sensor package 300. Thus, for example, the redistribution layer 332 (which, as shown, may include multiple sub-layers) may define a ball grid array of solder balls along a bottom side of the integrated sensor package 300, thereby facilitating simple soldering and/or reflow processes to conductively couple the integrated sensor package 300 to a circuit board or other component.

The integrated sensor package 300 may also include a redistribution layer on the top side of the integrated sensor package 300. FIG. 4, for example, illustrates a dielectric layer 329 (which may be a passivation layer) on the top side of the integrated sensor package. (As noted above, the "top" surface in FIG. 4 may face outwardly through a rear surface of a device such as a smartwatch.) The dielectric layer 329 may also define holes that coincide with or are aligned with the holes of the mask 326 to allow optical access to the optical components of the integrated sensor package 300. While conductive traces are not shown in the cross-section of FIG. 4, conductive traces of a top-side redistribution layer are shown schematically in FIG. 5. FIG. 4 also shows a mask 311 on the bottom side of the integrated sensor package 300. The mask 311 may be formed of the same or similar material as the mask 326, and may help prevent oxidization of the conductive traces and prevent accidental shorting of the conductive traces during soldering or other operations.

Figure 5:
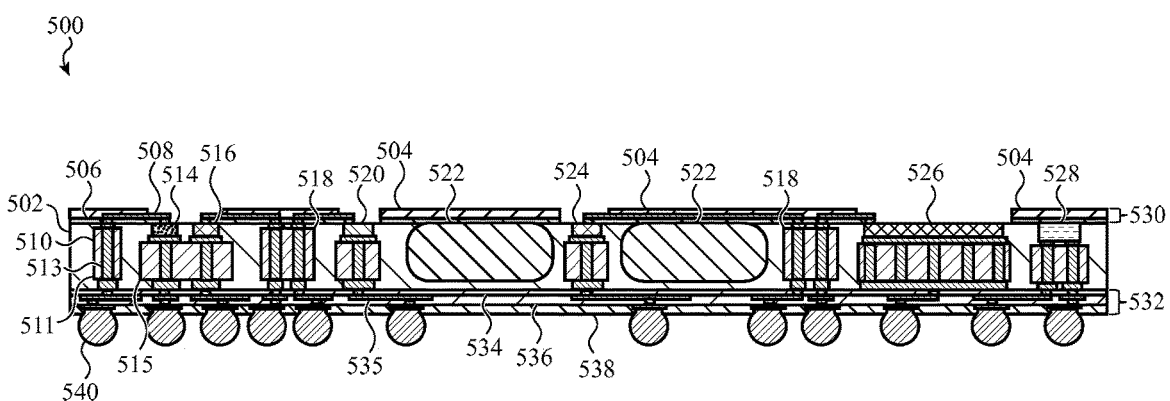
FIG. 5 depicts a schematic cross-sectional view of an example integrated sensor package.

FIG. 5 is a schematic cross-sectional view of an integrated sensor package 500. While the components in the integrated sensor package 500 are not in the same positions as the components in the integrated sensor package 300, the integrated sensor package 500 is provided to illustrate examples of a variety of different components that may be included in an integrated sensor package, as well as how they may be at least partially encapsulated in a matrix material and interconnected using redistribution layers.

The integrated sensor package 500 includes a variety of components that are at least partially encapsulated in a matrix material 502. The matrix material 502 may be a cured epoxy or another suitable material (e.g., a nonconductive material that can be flowed or otherwise introduced onto the components and then hardened or cured). The integrated sensor package 500 may include components such as a permanent magnet 522 (which, as noted above, may represent multiple permanent magnets), LEDs 514, 516, and 524, a photodiode 526, via structures 510, 518, and an additional component 528 (which may be a circuit element (e.g., a capacitor, inductor, etc.), a processor, an integrated circuit, a surface-mount component, or any other suitable electrical component. In some cases, the additional component 528 may be an application-specific integrated circuit (ASIC), analog and/or passive circuit components (e.g., inductors, capacitors, resistors, etc.), heat sinks, mechanical stiffening members, reinforcing members, or the like. Heat sinks and/or mechanical stiffening/reinforcing members may be formed from or include materials such as copper, stainless steel, nickel, ceramics (e.g., Si3N4, SiO2, AlOx, AlN), or the like.

As shown in FIG. 5, in some cases more than one component may be coupled to one carrier. For example, both LEDs 514 and 516 may be coupled to a single carrier 515. In some cases, the LEDs 514, 516 correspond to LEDs 306 and 308 of the integrated sensor package 300 of FIG. 3A. LEDs 520 and 524 (which may correspond to LEDs 312 and 314, respectively, in the integrated sensor package 300) may be coupled to their own distinct carriers. Whether components share carriers or are coupled to their own carrier may depend on factors such as the thickness of the components, the proximity of the components to one another in the integrated sensor package, electrical and/or cooling requirements of the components, or the like.

The photodiode 526 may correspond to the photodiodes 304 of the integrated sensor package 300. Details of the photodiodes 304 therefore apply equally to the photodiode 526, and for brevity those details are not repeated here.

The integrated sensor package 500 also includes via structures 510, 518. The via structures may include carriers (e.g., the carrier 511 of the via structure 510) and conductive vias extending through the carriers (e.g., the conductive via 513 of the via structure 510). While the carrier and conductive vias of the via structures 518 are not separately labeled, the details of the carrier 511 and conductive via 513 apply equally to those of the via structures 518. Further, the carrier 511 and conductive via 513 may be embodiments of the carriers 338 and conductive vias 340 in FIG. 4, and the details of those components therefore apply equally to the carrier 511 and conductive via 513. For brevity those details are not repeated here.

The via structures may include a single conductive via, as shown in the via structure 510, or multiple conductive vias, as shown in the via structures 518 (which each include two conductive vias, though more are also contemplated). The via structures may be used to conductively couple electrical components such as integrated circuit dies, photodiodes, LEDs, and the like, which may be positioned proximate a first side of the integrated sensor package 500, to a redistribution layer on the opposite side of the integrated sensor package 500. To that end, conductive members (e.g., conductive traces of the redistribution layers on the first and second sides of the intergrade sensor package) may be conductively coupled to the ends of the via structures.

In some cases, instead of or in addition to encapsulating pre-fabricated via structures in a matrix material, vias may be formed by forming holes in and/or through a matrix material after it has been at least partially cured, and positioning conductive material in the hole (e.g., conductive rods, conductive plating along the holes' surfaces).

The integrated sensor package 500 also includes a first redistribution layer 530 on a first (e.g., top) side of the body structure (e.g., the cured matrix material 502), and a second redistribution layer 532 on a second (e.g., bottom) side of the body structure. The first and second redistribution layers 530, 532 are configured to conductively couple the components of the integrated sensor package 500 via conductive traces and dielectric layers. For example, the first redistribution layer includes at least one dielectric layer (e.g., the dielectric layer 506) and conductive traces (e.g., the conductive trace 508 conductively coupling the LED 514 to the via structure 510). The second redistribution layer 532 may also include at least one dielectric layer (e.g., the dielectric layers 534, 536) and conductive traces (e.g., the conductive traces 535). The first redistribution layer 530 may be used to conductively couple the components of the integrated sensor package 500 to one another and/or to via structures, and the second redistribution layer 532 may be used to conductively couple the components and/or via structures to solder balls (e.g., the solder ball 540), or other conductive pads or surfaces, which may in turn be conductively coupled to other circuit boards, wires, or conductors of a device. The second redistribution layer 532 may also allow the solder balls 540 to be positioned in locations other than directly below the electrical components to which they are conductively coupled, thereby allowing the solder balls 540 (or solder pads) to be positioned in a more suitable spatial distribution, such as a grid.

The integrated sensor package 500 may also include a first mask 504, which may be positioned over the first redistribution layer 530, and a second mask 538, which may be positioned over the second redistribution layer 532. The first and second masks 504, 538 may be opaque, and may be formed of ink, dye, solder mask materials, epoxy, sheets or films, coatings, or the like. The masks may be a single layer of material, or multiple layers, and may define holes that are positioned over the photodiodes, LEDs, and conductive traces to which the solder balls are attached.

Figure 6A:
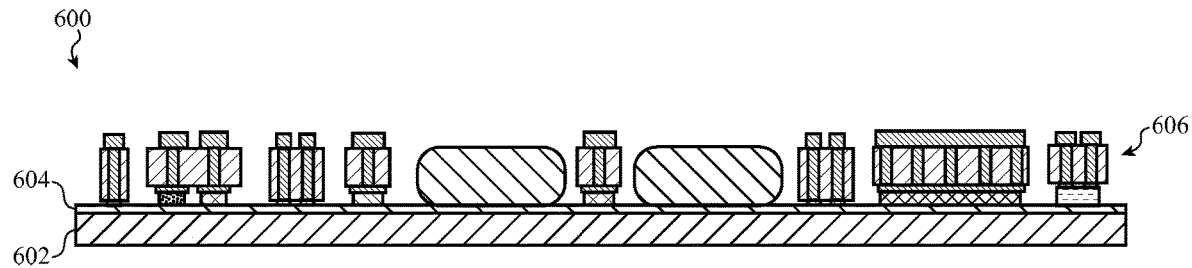
FIGS. 6A-6F depict schematic cross-sectional views of the integrated sensor package of FIG. 5 at various stages of manufacturing.
Figure 6B:
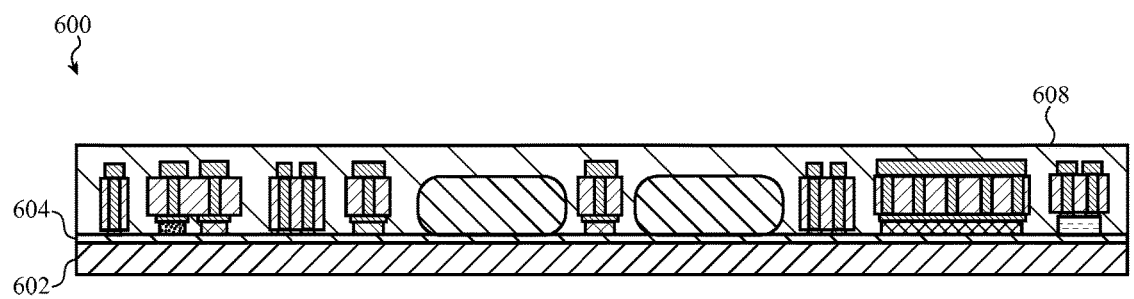

FIGS. 6A-6F illustrate an integrated sensor package at various stages of an assembly or production process. In FIG. 6A, components 606 of the integrated sensor package 600 are coupled to a carrier wafer 602 via an adhesive 604. The carrier wafer 602 may be formed from glass, silicon, or any other suitable material, such as a ceramic, polymer, metal, or the like. The adhesive 604 may be a double-sided tape, adhesive film, or the like.

The components 606 are coupled to the carrier wafer 602 in the intended final arrangement for the integrated sensor package 600. Thus, for example, the permanent magnet may be positioned in a central region, an array of photodiodes may be positioned about the outer periphery of the permanent magnet, and an array of LEDs may be positioned about the outer periphery of the permanent magnet. Other components, such as via structures, may be positioned in their intended final positions. The components 606 may be positioned such that the sides that are intended to be exposed (e.g., without overlying matrix material to interfere with the emission or receipt of light) are facing and/or in contact with the adhesive 604. In this way, when the adhesive 604 and carrier wafer 602 are removed, the active sides of the components 606 are not covered by matrix material.

Once the components 606 are arranged and coupled to the carrier wafer 602, a matrix material 608 (FIG. 6B) may be flowed or otherwise introduced over the components 606. The matrix material 608 may at least partially encapsulate the components 606, and may flow into a hole defined in the permanent magnet (as described above), thereby at least partially encapsulating components positioned in the hole. As noted above, the matrix material 608 may be a flowable epoxy or other suitable material. In some cases, a mold may be used to form and contain the matrix material 608 in a desired shape. For example, a mold may be positioned such that the components 606 are within a mold cavity having a desired shape and size, and the matrix material 608 may be introduced into the mold cavity. When the matrix material 608 is in place, and optionally in a mold, it may be at least partially cured (e.g., hardened) to form a body structure of the integrated sensor package 600. The mold may also apply a pressure to the matrix material 608 during the forming and/or curing processes (e.g., a compression molding process may be used). Curing the matrix material 608 may include allowing the matrix material 608 to cure at ambient temperature and conditions. In some cases, the matrix material 608 may be heated, exposed to particular light or radiation (e.g., ultraviolet light), or otherwise subjected to additional curing operations.

Once the matrix material 608 is at least partially cured (and optionally fully cured), the carrier wafer 602 and the adhesive 604 may be removed from the matrix material 608. This may include using mechanical and/or chemical means (e.g., a solvent) to remove or dissolve the adhesive. Before or after the carrier wafer 602 and adhesive 604 are removed, the matrix material 608 may be fully cured and the surface of the integrated sensor package 600 from which the adhesive was removed may be subject to surface treatments, such as polishing, washing, cleaning, or the like.

Figure 6C:
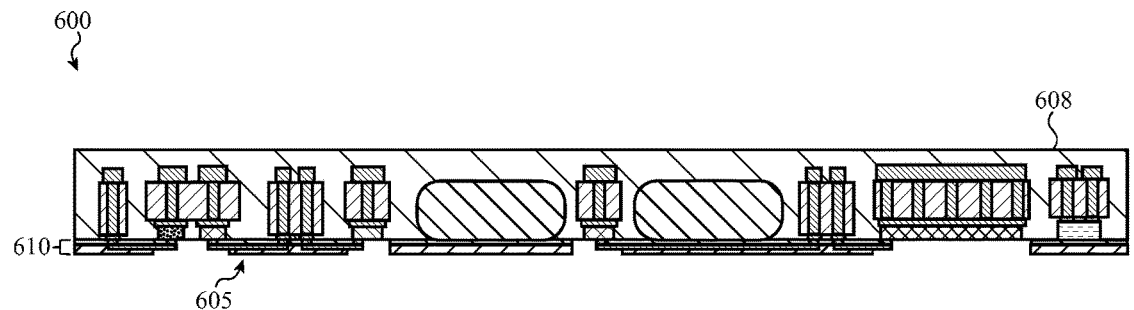

As shown in FIG. 6C, a first redistribution layer 610 may be formed on a first side 605 of the integrated sensor package 600. The redistribution layer 610 may include one or more sub-layers, which may include dielectric layers and conductive traces, as described above. A mask, shown in FIG. 6C as part of the redistribution layer 610, may also be applied. The dielectric layers may be formed by passivation processes or deposition processes such as chemical vapor deposition, plasma vapor deposition, or the like. The conductive traces may be formed via sputtering, printing, photolithography, or other suitable deposition or formation techniques. The first redistribution layer 610 may conductively couple components of the integrated sensor package 600 along the first side of the integrated sensor package 600 (e.g., the side that is intended to face towards the exterior of a device such as a smartwatch).

Figure 6D:
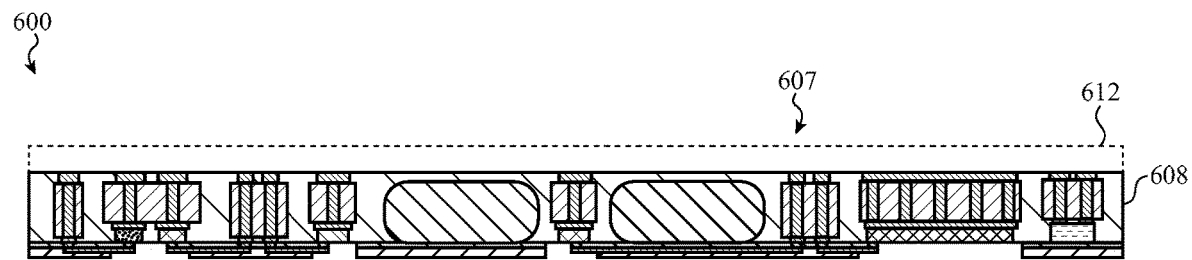

As shown in FIG. 6D, a portion of the matrix material 608 (e.g., the portion 612) may be removed from a second side of the integrated sensor package 600 to expose conductive pads on a second side 607 of the integrated sensor package 600. The matrix material 608 may be removed using grinding, polishing, machining, or other suitable material removal operations. The removal of the portion 612 of the matrix material 608 may also ensure a substantially flat surface along the second side of the integrated sensor package 600, and also help produce a uniform thickness of the body structure.

Figure 6E:
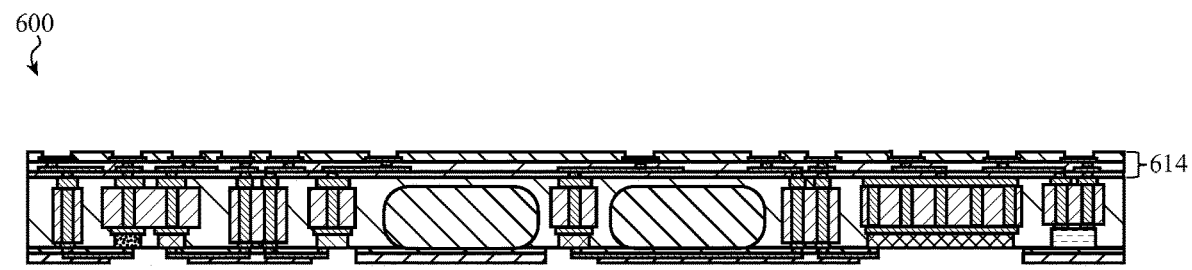
Figure 6F:
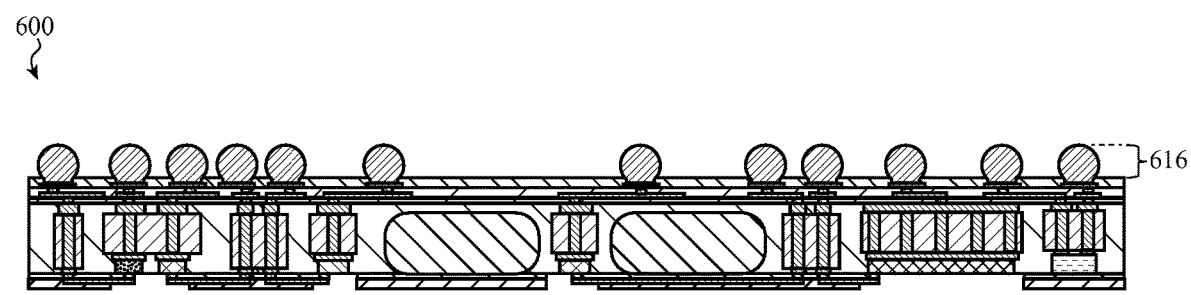

After removal of the portion of the matrix material 608 to expose the conductive pads of the components along the second side of the integrated sensor package 600, a second redistribution layer 614 may be formed, as shown in FIG. 6E. As noted above, the second redistribution layer 614 may conductively couple the components of the integrated sensor package 600 to solder balls 616, as shown in FIG. 6F. In some cases, instead of or in addition to the solder balls 616, the second redistribution layer 614 may include solder pads or other conductive members to facilitate conductive coupling to circuit boards or the like. The second redistribution layer 614 may include multiple sub-layers, as described above, such as multiple dielectric layers and conductive traces. A mask, shown in FIG. 6C as part of the redistribution layer 610, may also be applied. The second redistribution layer 614 may be formed in the same or similar manner as the first redistribution layer 610. The completed integrated sensor package 600, as shown in FIG. 6F, may then be conductively coupled to a circuit board or other component of a device, as described above.

In cases where vias are formed through the matrix material 608, holes for the vias may be formed after the matrix material 608 is at least partially cured. The holes may be formed by laser drilling, mechanical punching, or the like. The holes may then be plated and/or at least partially filled with a conductive material. Conductive pads or rings may then be applied to the first and second sides of the matrix material and in contact with the conductive material to complete the vias, which may then be conductively coupled to the components 606 when the redistribution layers are formed.

While FIGS. 6A-6F illustrate a schematic view of a single, discrete integrated sensor package, the same or similar manufacturing process may be used to form multiple integrated sensor packages on a single carrier wafer. In such cases, after the integrated sensor package 600 is completed (e.g., at the stage shown in FIG. 6F), a singulation process may be performed to cut through the matrix material to form individual sensor packages. Singulation may be performed by laser singulation, mechanical cutting operations (e.g., a saw), water jet, or the like.

Figure 7:
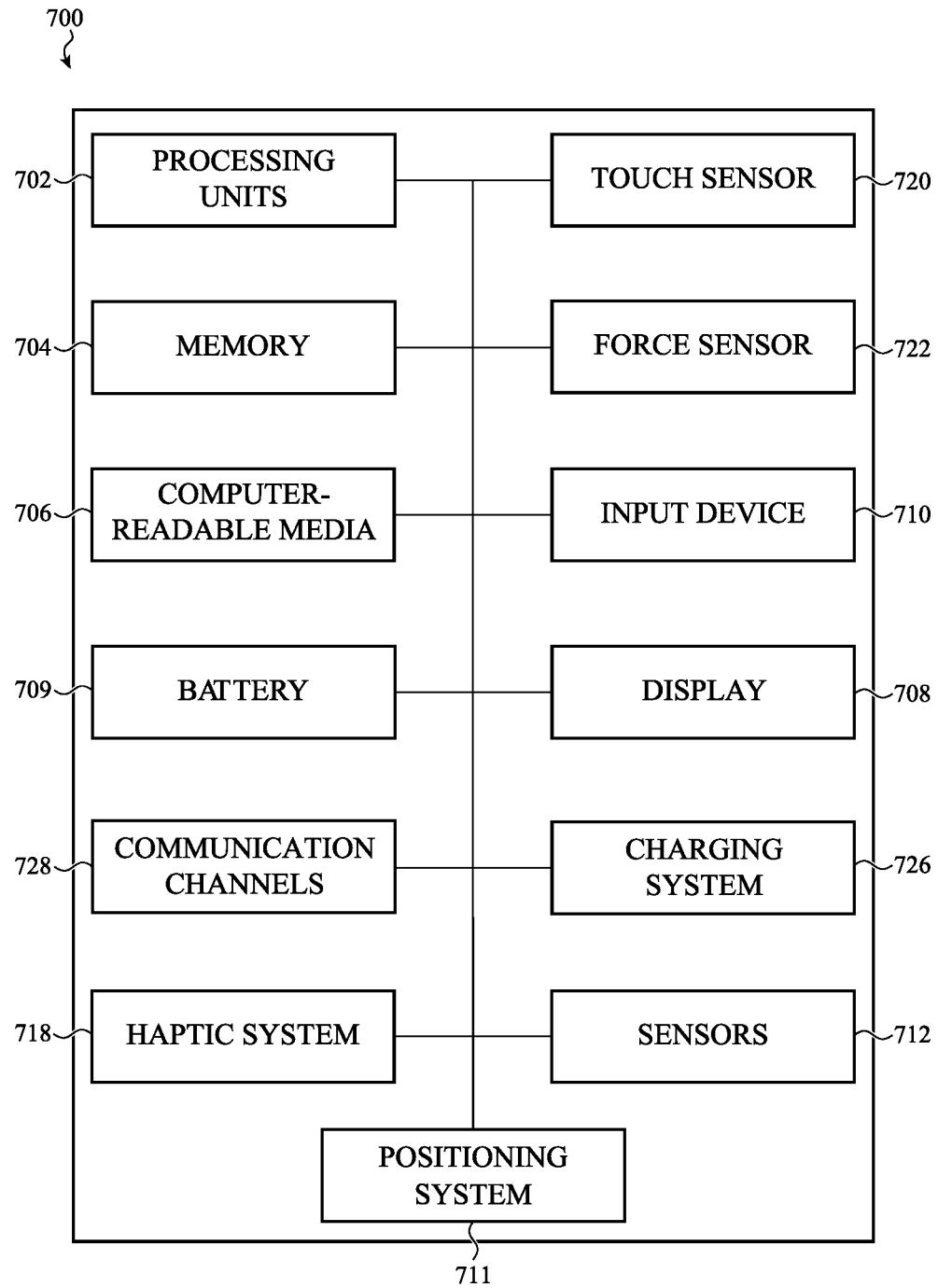
FIG. 7 depicts a schematic diagram of an example electronic device.

FIG. 7 depicts an example schematic diagram of an electronic device 700. By way of example, the device 700 of FIG. 7 may correspond to the electronic device 100 shown in FIGS. 1A-2, or to any other electronic device that may include an integrated sensor package as described herein. For example, the device 700 may be a wearable electronic device (e.g., a watch, smartwatch, fitness tracker, biometric sensing device), a mobile phone, a stylus, a tablet computer, a case for storing an electronic device (e.g., an earbud storage and charging case), a laptop computer, a wirelessly locatable device, or the like.

As shown in FIG. 7, a device 700 includes a processing unit 702 operatively connected to computer memory 704 and/or computer-readable media 706. The processing unit 702 may be operatively connected to the memory 704 and computer-readable media 706 components via an electronic bus or bridge. The processing unit 702 may include one or more computer processors or microcontrollers that are configured to perform operations in response to computer-readable instructions. The processing unit 702 may include the central processing unit (CPU) of the device. Additionally or alternatively, the processing unit 702 may include other processors within the device including application specific integrated chips (ASIC) and other microcontroller devices.

The memory 704 may include a variety of types of non-transitory computer-readable storage media, including, for example, read access memory (RAM), read-only memory (ROM), erasable programmable memory (e.g., EPROM and EEPROM), or flash memory. The memory 704 is configured to store computer-readable instructions, sensor values, and other persistent software elements. Computer-readable media 706 also includes a variety of types of non-transitory computer-readable storage media including, for example, a hard-drive storage device, a solid-state storage device, a portable magnetic storage device, or other similar device. The computer-readable media 706 may also be configured to store computer-readable instructions, sensor values, and other persistent software elements.

In this example, the processing unit 702 is operable to read computer-readable instructions stored on the memory 704 and/or computer-readable media 706. The computer-readable instructions may adapt the processing unit 702 to perform the operations or functions described above. For example, the processing unit 702, the memory 704, and/or the computer-readable media 706 may be configured to operate an optical sensor that employs an integrated sensor package as described above. The computer-readable instructions may be provided as a computer-program product, software application, or the like.

As shown in FIG. 7, the device 700 also includes a display 708. The display 708 may include a liquid-crystal display (LCD), an organic light emitting diode (OLED) display, a light emitting diode (LED) display, or the like. If the display 708 is an LCD, the display 708 may also include a backlight component that can be controlled to provide variable levels of display brightness. If the display 708 is an OLED or LED type display, the brightness of the display 708 may be controlled by modifying the electrical signals that are provided to display elements. The display 708 may correspond to any of the displays shown or described herein.

The device 700 may also include a battery 709 that is configured to provide electrical power to the components of the device 700. The battery 709 may include one or more power storage cells that are linked together to provide an internal supply of electrical power. The battery 709 may be operatively coupled to power management circuitry that is configured to provide appropriate voltage and power levels for individual components or groups of components within the device 700. The battery 709 may store received power so that the device 700 may operate without connection to an external power source for an extended period of time, which may range from several hours to several days.

In some embodiments, the device 700 includes one or more input devices 710. An input device 710 is a device that is configured to receive user input. The one or more input devices 710 may include, for example, a crown input system, a push button, a touch-activated button, a keyboard, a key pad, or the like (including any combination of these or other components). In some embodiments, the input device 710 may provide a dedicated or primary function, including, for example, a power button, volume buttons, home buttons, scroll wheels, and camera buttons.

The device 700 may also include a touch sensor 720 that is configured to determine a location of a touch on a touch-sensitive surface of the device 700 (e.g., an input surface defined by the portion of a cover 108 that covers a display 109). The touch sensor 720 may use or include capacitive sensors, resistive sensors, surface acoustic wave sensors, piezoelectric sensors, strain gauges, or the like. In some cases the touch sensor 720 associated with a touch-sensitive surface of the device 700 may include a capacitive array of electrodes or nodes that operate in accordance with a mutual-capacitance or self-capacitance scheme. The touch sensor 720 may be integrated with one or more layers of a display stack (e.g., the display 109) to provide the touch-sensing functionality of a touchscreen.

The device 700 may also include a force sensor 722 that is configured to receive and/or detect force inputs applied to a user input surface of the device 700 (e.g., the display 109). The force sensor 722 may use or include capacitive sensors, resistive sensors, surface acoustic wave sensors, piezoelectric sensors, strain gauges, or the like. In some cases, the force sensor 722 may include or be coupled to capacitive sensing elements that facilitate the detection of changes in relative positions of the components of the force sensor (e.g., deflections caused by a force input). The force sensor 722 may be integrated with one or more layers of a display stack (e.g., the display 109) to provide force-sensing functionality of a touchscreen.

The one or more communication channels 728 may include one or more wireless interface(s) that are adapted to provide communication between the processing unit(s) 702 and an external device. The one or more communication channels 728 may include antennas (e.g., antennas that include or use the housing members of a housing as radiating members), communications circuitry, firmware, software, or any other components or systems that facilitate wireless communications with other devices. In general, the one or more communication channels 728 may be configured to transmit and receive data and/or signals that may be interpreted by instructions executed on the processing unit(s) 702. In some cases, the external device is part of an external communication network that is configured to exchange data with wireless devices. Generally, the wireless interface may communicate via, without limitation, radio frequency, optical, acoustic, and/or magnetic signals and may be configured to operate over a wireless interface or protocol. Example wireless interfaces include radio frequency cellular interfaces (e.g., 2G, 3G, 4G, 4G long-term evolution (LTE), 5G, GSM, CDMA, or the like), fiber optic interfaces, acoustic interfaces, Bluetooth interfaces, infrared interfaces, USB interfaces, Wi-Fi interfaces, TCP/IP interfaces, network communications interfaces, or any conventional communication interfaces. The one or more communication channels 728 may also include ultra-wideband interfaces, which may include any appropriate communications circuitry, instructions, and number and position of suitable UWB antennas.

The device 700 may also include a haptic output system 718. The haptic output system 718 may be configured to produce haptic outputs that are detectable by a user of the device, such as vibrations, oscillations, pulses, translations, or the like. The haptic output system may include any suitable actuators and/or devices that produce haptic outputs, such as linear actuators, resonant linear actuators, solenoids, voice coil motors, reluctance force actuators, or the like.

The device 700 may also include a charging system 726 that charges the battery 709 of the device. The charging system 726 may be configured to wirelessly receive power via an inductive coupling between an inductive coil in the device 700 and an output coil of a charger, as described herein. In some cases, the coil of a charging system may be part of an integrated sensor package, as described herein (e.g., it may be at least partially encapsulated in a common matrix material that defines the principal structural body of a component that includes sensor components, an inductive coil, and optionally a permanent magnet for removably coupling the device 700 to a docking device external to the device 700).

The device 700 may also include a positioning system 711. The positioning system 711 may be configured to determine the location of the device 700. For example, the positioning system 711 may include magnetometers, gyroscopes, accelerometers, optical sensors, cameras, global positioning system (GPS) receivers, inertial positioning systems, or the like. The positioning system 711 may be used to determine spatial parameters of the device 700, such as the location of the device 700 (e.g., geographical coordinates of the device), measurements or estimates of physical movement of the device 700, an orientation of the device 700, or the like.

The device 700 may also include one or more additional sensors 712 to receive inputs (e.g., from a user or another computer, device, system, network, etc.) or to detect any suitable property or parameter of the device, the environment surrounding the device, people or things interacting with the device (or nearby the device), or the like. For example, a device may include temperature sensors, biometric sensors (e.g., fingerprint sensors, optical sensing systems, blood-oxygen sensors, blood sugar sensors, electrocardiographs, or the like), eye-tracking sensors, retinal scanners, humidity sensors, buttons, switches, or the like.

To the extent that multiple functionalities, operations, and structures described with reference to FIG. 7 are disclosed as being part of, incorporated into, or performed by the device 700, it should be understood that various embodiments may omit any or all such described functionalities, operations, and structures. Thus, different embodiments of the device 700 may have some, none, or all of the various capabilities, apparatuses, physical features, modes, and operating parameters discussed herein. Further, the systems included in the device 700 are not exclusive, and the device 700 may include alternative or additional systems, components, modules, programs, instructions, or the like, that may be necessary or useful to perform the functions described herein.

As described above, one aspect of the present technology is the gathering and use of data available from various sources, such as to provide health-related or other personal information to the user. The present disclosure contemplates that in some instances, this gathered data may include personal information data that uniquely identifies or can be used to contact or locate a specific person. Such personal information data can include demographic data, location-based data, telephone numbers, email addresses, twitter ID's, home addresses, data or records relating to a user's health or level of fitness (e.g., vital signs measurements, medication information, exercise information), date of birth, or any other identifying or personal information.

The present disclosure recognizes that the use of such personal information data, in the present technology, can be used to the benefit of users. For example, the personal information data can be used to deliver or provide health-related information that is of greater interest to the user. Further, other uses for personal information data that benefit the user are also contemplated by the present disclosure. For instance, health and fitness data may be used to provide insights into a user's general wellness, or may be used as positive feedback to individuals using technology to pursue wellness goals.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the US, collection of or access to certain health data may be governed by federal and/or state laws, such as the Health Insurance Portability and Accountability Act (HIPAA); whereas health data in other countries may be subject to other regulations and policies and should be handled accordingly. Hence different privacy practices should be maintained for different personal data types in each country.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case of advertisement delivery services, the present technology can be configured to allow users to select to "opt in" or "opt out" of participation in the collection of personal information data during registration for services or anytime thereafter. In another example, users can select not to provide mood-associated data for targeted content delivery services. In yet another example, users can select to limit the length of time mood-associated data is maintained or entirely prohibit the development of a baseline mood profile. In addition to providing "opt in" and "opt out" options, the present disclosure contemplates providing notifications relating to the access or use of personal information. For instance, a user may be notified upon downloading an app that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing specific identifiers (e.g., date of birth, etc.), controlling the amount or specificity of data stored (e.g., collecting location data at a city level rather than at an address level), controlling how data is stored (e.g., aggregating data across users), and/or other methods.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, content can be selected and delivered to users by inferring preferences based on non-personal information data or a bare minimum amount of personal information, such as the content being requested by the device associated with a user, other non-personal information available to the content delivery services, or publicly available information.

As used herein, the phrase "at least one of" preceding a series of items, with the term "and" or "or" to separate any of the items, modifies the list as a whole, rather than each member of the list. The phrase "at least one of" does not require selection of at least one of each item listed; rather, the phrase allows a meaning that includes at a minimum one of any of the items, and/or at a minimum one of any combination of the items, and/or at a minimum one of each of the items. By way of example, the phrases "at least one of A, B, and C" or "at least one of A, B, or C" each refer to only A, only B, or only C; any combination of A, B, and C; and/or one or more of each of A, B, and C. Similarly, it may be appreciated that an order of elements presented for a conjunctive or disjunctive list provided herein should not be construed as limiting the disclosure to only that order provided.

The foregoing description, for purposes of explanation, used specific nomenclature to provide a thorough understanding of the described embodiments. However, it will be apparent to one skilled in the art that the specific details are not required in order to practice the described embodiments. Thus, the foregoing descriptions of the specific embodiments described herein are presented for purposes of illustration and description. They are not targeted to be exhaustive or to limit the embodiments to the precise forms disclosed. It will be apparent to one of ordinary skill in the art that many modifications and variations are possible in view of the above teachings. Also, when used herein to refer to positions of components, the terms above, below, over, under, left, or right (or other similar relative position terms), do not necessarily refer to an absolute position relative to an external reference, but instead refer to the relative position of components within the figure being referred to. Similarly, horizontal and vertical orientations may be understood as relative to the orientation of the components within the figure being referred to, unless an absolute horizontal or vertical orientation is indicated.

What is claimed is:

1. An integrated sensor package for an electronic device, comprising:
   a matrix material defining a body structure of the integrated sensor package;
   a light emitting diode at least partially encapsulated in the matrix material;
   a photodiode at least partially encapsulated in the matrix material and configured to detect light emitted by the light emitting diode and reflected by an object external to the integrated sensor package;
   a via structure at least partially encapsulated in the matrix material;
   a permanent magnet at least partially encapsulated in the matrix material;
   a first conductive member on a first side of the integrated sensor package and conductively coupling the light emitting diode to a first end of the via structure; and a second conductive member on a second side of the integrated sensor package opposite the first side and conductively coupled to a second end of the via structure.

2. The integrated sensor package of claim 1, wherein the light emitting diode and the photodiode are configured to operate as an optical emitter-receiver pair for an optical sensing system.

3. The integrated sensor package of claim 1, wherein:
the permanent magnet defines a hole extending through a body of the permanent magnet;
the integrated sensor package further comprises an electronic component at least partially within the hole defined in the permanent magnet; and
the matrix material extends into the hole defined in the permanent magnet and at least partially encapsulates the electronic component.

4. The integrated sensor package of claim 1, wherein:
the first conductive member is a first conductive trace; and
the second conductive member is a second conductive trace.

5. The integrated sensor package of claim 4, wherein:
the integrated sensor package further comprises:
a first dielectric layer on a first surface of the body structure of the integrated sensor package; and
a second dielectric layer on a second surface of the body structure, the second surface opposite the first surface;
the first conductive trace is positioned on the first dielectric layer; and
the second conductive trace is positioned on the second dielectric layer.

6. The integrated sensor package of claim 5, further comprising:
a third dielectric layer positioned on the second dielectric layer; and
a third conductive trace positioned on the third dielectric layer and conductively coupled to the second conductive trace.

7. The integrated sensor package of claim 1, further comprising a solder ball soldered to the second conductive member.

8. A wearable electronic device comprising:
a housing member at least partially defining an internal volume of the wearable electronic device;
a front cover coupled to the housing member;
a display positioned under the front cover; and
an integrated sensor package within the internal volume of the wearable electronic device and comprising:
a matrix material defining a body structure of the integrated sensor package;
an integrated circuit at least partially encapsulated in the matrix material; and
a permanent magnet at least partially encapsulated in the matrix material and configured to magnetically align the wearable electronic device with a docking device external to the wearable electronic device.

9. The wearable electronic device of claim 8, wherein:
the integrated sensor package further comprises a light emitting diode at least partially encapsulated in the matrix material; and
the integrated circuit is a photodiode configured to detect light emitted by the light emitting diode and reflected by a wearer of the wearable electronic device.

10. The wearable electronic device of claim 9, wherein:
the wearable electronic device further comprises a rear cover coupled to the housing member and configured to contact a body of the wearer of the wearable electronic device when the wearable electronic device is being worn, the rear cover defining:
a first surface defining an exterior surface of the wearable electronic device; and
a second surface opposite the first surface;
the integrated sensor package is attached to the second surface of the rear cover;
the light emitting diode is configured to direct the light through the rear cover; and
the photodiode is configured to detect the light through the rear cover.

11. The wearable electronic device of claim 10, further comprising an inductive coil within the internal volume of the wearable electronic device and configured to wirelessly receive power from the docking device, through the rear cover, when the wearable electronic device is magnetically attached to the docking device.

12. The wearable electronic device of claim 11, wherein the inductive coil is positioned around an outer periphery of the integrated sensor package.

13. The wearable electronic device of claim 9, wherein the light emitting diode and the photodiode are components of an optical sensing system of the wearable electronic device.

14. The wearable electronic device of claim 8, further comprising a passive circuit component at least partially encapsulated in the matrix material.

15. An integrated sensor package for an optical sensing system of an electronic device, comprising:
a matrix material defining a body structure of the integrated sensor package;
an array of light emitting diodes positioned around a central region of the body structure, the light emitting diodes of the array of light emitting diodes at least partially encapsulated in the matrix material;
an array of photodiodes positioned around the central region of the body structure, the photodiodes of the array of photodiodes at least partially encapsulated in the matrix material; and
a permanent magnet positioned in the central region of the body structure and at least partially encapsulated in the matrix material.

16. The integrated sensor package of claim 15, wherein the permanent magnet is a neodymium iron boron magnet having a thickness of about 500 microns or less.

17. The integrated sensor package of claim 15, wherein:
the integrated sensor package further comprises:
a substrate at least partially encapsulated in the matrix material; and
a via extending through the substrate from a first surface of the substrate to a second surface of the substrate; and
a photodiode of the array of photodiodes is coupled to the substrate and conductively coupled to the via.

18. The integrated sensor package of claim 15, wherein the array of light emitting diodes comprises:
a first light emitting diode configured to emit visible light; and
a second light emitting diode configured to emit infrared light.

19. The integrated sensor package of claim 15, further comprising:
a via structure at least partially encapsulated in the matrix material;

a first conductive trace on a first side of the integrated sensor package and conductively coupling a photodiode of the array of photodiodes to a first end of the via structure; and a second conductive trace on a second side of the integrated sensor package and conductively coupled to a second end of the via structure.

20. The integrated sensor package of claim 19, further comprising:

a first dielectric layer between the matrix material and the first conductive trace; and a second dielectric layer between the matrix material and the second conductive trace.

\* \* \* \* \*